United States Patent [19]

Borzone

[11] Patent Number: 5,242,447
[45] Date of Patent: Sep. 7, 1993

[54] PIN WITH TAPERED ROOT DIAMETER

[75] Inventor: Rocco R. Borzone, Emerson, N.J.

[73] Assignee: Howmedica Inc., New York, N.Y.

[21] Appl. No.: 832,110

[22] Filed: Feb. 6, 1992

[51] Int. Cl.$^5$ .................................................. A61F 5/04
[52] U.S. Cl. ........................................ 606/73; 411/386;
606/59
[58] Field of Search ...................... 606/59, 63, 73, 72,
606/104; 411/426, 387, 386, 418

[56] References Cited

U.S. PATENT DOCUMENTS

| 74,489 | 2/1868 | Bidwell | 411/386 |
| 3,045,523 | 7/1962 | Reed | 411/387 |
| 4,463,753 | 8/1984 | Gustillo | 606/73 |
| 4,978,350 | 12/1990 | Wagenknecht | 606/73 |

Primary Examiner—Robert A. Hafer
Assistant Examiner—David J. Kenealy
Attorney, Agent, or Firm—Robert D. Schaffer

[57] ABSTRACT

A pin is disclosed that includes an elongated shaft having a constant diameter, and an elongated threaded portion having first and second axially separated ends, the first axial end being axially closer to the elongated shaft than the second axial end. The threaded portion has a root diameter that tapers linearly from a maximum value at the first axial end to a minimum value at the second axial end. The root diameter at the first axial end is substantially equal to the diameter of the elongated shaft itself. The pin also includes a drill end extending axially from the second axial end of the threaded portion such that the drill end is connected to the elongated shaft by the threaded portion. Also disclosed is a preferred method of forming the threaded portion on the pin including the steps of: rotating the pin about its longitudinal axis; moving a cutting surface at a predetermined speed across an axial portion of the rotating pin to thereby cut threads in the axial portion; and linearly increasing the distance between the cutting surface and the longitudinal axis of the pin as the cutting surface is moved across the axial portion of the pin.

11 Claims, 1 Drawing Sheet

PIN WITH TAPERED ROOT DIAMETER

FIELD OF THE INVENTION

This invention relates to a pin used to penetrate a bone, and, more particularly, to a guide pin having an improved threaded portion used to facilitate the placement of a bone screw.

BACKGROUND OF THE INVENTION

Bone screws are widely used to secure a fractured bone in place while the bone heals. For example, when a bone breaks, the two pieces of the broken bone usually become misaligned making it difficult for the bone to heal properly. Although a surgeon can manipulate the pieces of the broken bone back into alignment, there is a tendency for the pieces of bone to again become misaligned during the lengthy healing process due to movement by the patient. Surgeons therefore often use bone screws to screw the pieces of the broken bone together, reducing the likelihood that the bone pieces will move during the healing process.

In order to provide sufficient strength and support to keep the bone pieces in place while the bone heals, bone screws typically have diameters in excess of 4.5 millimeters. For example, the diameter of a bone screw commonly used to engage the cortical bone is 4.5 millimeters, while a 5.0 millimeter bone screw is used to engage the cancellous bone.

Due to the difficulty associated with placing such large diameter bone screws into a fractured bone, smaller diameter guide pins are used to initially immobilize the fractured bones, and to then guide the larger bone screws into place. One commonly used guide pin, having a diameter of about 2.0 millimeters, is illustrated in FIG. 1, and includes an elongated shaft or shank 12 (only a portion of which is shown in FIG. 1), a threaded portion 14 and a drill end 16.

A surgeon will first align the pieces of the fractured bone, and then screw the guide pin into the fractured bone using the drill end 16 and the threads 14 to advance the guide pin into the bone. A cannulated bone screw (i.e., a bone screw having a hollow center), with an inner diameter slightly larger than the diameter of the guide pin, is then placed over the guide pin, and is advanced along the guide pin toward the injured bone. When the bone screw reaches the bone, the bone screw is screwed into the bone, providing sufficient support for the bone to heal. Once the bone screw is in place, the guide pin is removed.

Therefore, the guide pin provides a guide for the movement of the bone screw and also serves to keep the bone pieces properly aligned while the bone screw is being screwed into the bone. Unfortunately, since the diameter of the guide pin is necessarily quite small, the forces exerted on the guide pin by the physician during placement of the guide pin, or subsequent placement of the bone screw, may cause the guide pin to fracture during the procedure at the point where the thread portion meets the shaft. The surgeon must then remove the broken pieces of the guide pin, and may need to begin the procedure again using a new guide pin.

SUMMARY OF THE INVENTION

A pin according to the present invention overcomes the disadvantages of the prior art by providing an improved threaded portion that increases the strength of the pin. The pin of the invention includes an elongated shaft having a constant diameter, and an elongated threaded portion having first and second axially separated ends, the first axial end being axially closer to the elongated shaft than the second axial end. The threaded portion has a root diameter that tapers from a maximum value at the first axial end to a minimum value at the second axial end.

In a preferred embodiment, the root diameter of the threaded portion tapers linearly and the first axial end of the threaded portion abuts the elongated shaft. The root diameter at the first axial end is substantially equal to the diameter of the elongated shaft itself. A preferred pin also includes a drill end extending axially from the second axial end of the threaded portion such that the drill end is connected to the elongated shaft by the threaded portion.

The threaded portion includes a plurality of threads, each of which are characterized by a thread height. The thread height of the threads increases linearly from the first axial end of the threaded portion to the second axial end. In a preferred pin the diameter of the elongated shaft is about two millimeters, and the thread diameter of the threaded portion is equal to the diameter of the elongated shaft.

Also disclosed is a preferred method of forming the threaded portion on the pin of the invention including the steps of: rotating the pin about its longitudinal axis; moving a cutting surface at a predetermined speed across an axial portion of the rotating pin to thereby cut threads in the axial portion; and increasing the distance between the cutting surface and the longitudinal axis of the pin as the cutting surface is moved across the axial portion of the pin. In a preferred embodiment the step of increasing the distance between the cutting surface and the longitudinal axis of the pin comprises increasing the distance linearly.

The present invention provides a substantial improvement in pins since the gradual tapering of the root diameter of the threaded portion eliminates the abrupt or sudden change in the diameter of the pin that is exhibited by the prior art. The sudden change in diameter at the junction of the threaded portion and the main shaft of prior art pins (see FIG. 1) creates a weak point that may fail under stress. The pin of this invention exhibits a gradual change in diameter and therefore includes no weak point. The advantages obtained include increased strength, improved ease of advancement of the pin into the bone, and a reduction in the heat generated by advancement of the pin into the bone. Other advantages will be apparent to those skilled in the art from the following detailed description of a preferred embodiment of the invention.

DETAILED DESCRIPTION OF A PREFERRED EMBODIMENT

Figure 2:
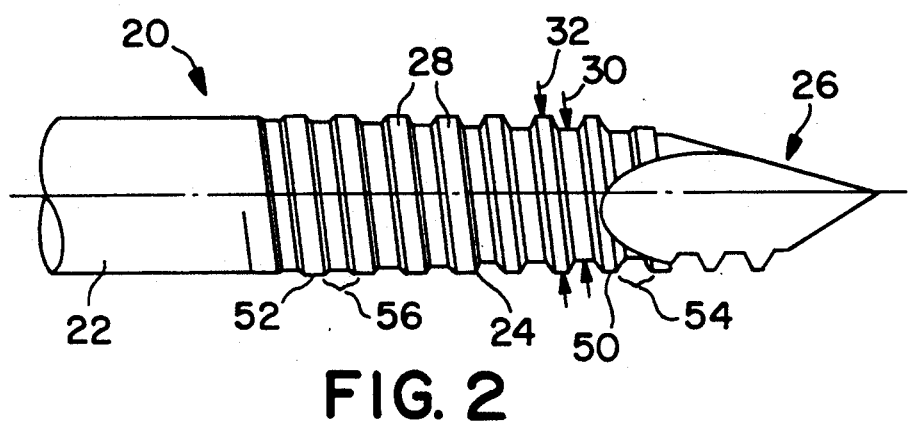
FIG. 2 is a side view of a guide pin according to the present invention.

Referring to FIG. 2, a guide pin 20, made according to the present invention, comprises an elongated shaft 22 (only a portion of which is shown in FIG. 2), a threaded portion 24 and a drill end 26. Threaded portion 24 includes a number of threads 28 and is characterized by a root diameter 30 and a thread diameter 32. The root diameter 30 is defined as the diameter of guide pin 20 at the root or base of each thread 28. The thread diameter 32 is equal to the diameter of guide pin 20 at the crest or highest point of each thread 28.

The thread diameter 32 is constant, and is equal to the diameter of shaft 22 (with the possible exception of a limited number of threads 28 whose surfaces have been altered due to the formation of drill end 26, as described below). The root diameter 30, however, gradually tapers from a maximum at the axial end of threaded portion 24 closest to shaft 22, to a minimum at the axial end of threaded portion 24 closest to drill end 26. The root diameter decreases linearly as a function of the axial distance from shaft portion 22.

As shown in FIG. 2, the pin is formed with threads having a constant pitch. However, because the root diameter gradually tapers from the shaft to the drill end, the outer portions of the threads 50, on the drill end widen as they progress along the longitudinal axis of the pin to the shaft. Thus, the outer portions of the threads 52 on the shaft end are wider than the outer portions of the threads 50 on the drill end. Due to this widening of the outer portions of the threads, the distance between the threads on the drill end 54 of the pin are smaller than the distance between the threads on the shaft end 56 of the pin. This decrease in the distance between the threads as the pin is screwed into the bone, for example, causes a continual compression of the bone along the longitudinal axis of the pin. Thus, as the pin progresses into the bone the bone is squeezed along two axes. The bone is squeezed perpendicular to the axis of the pin due to the increasing root diameter and the bone is squeezed along the longitudinal axis of the pin between the threads of the pin as the distance between the threads decreases.

Figure 3:
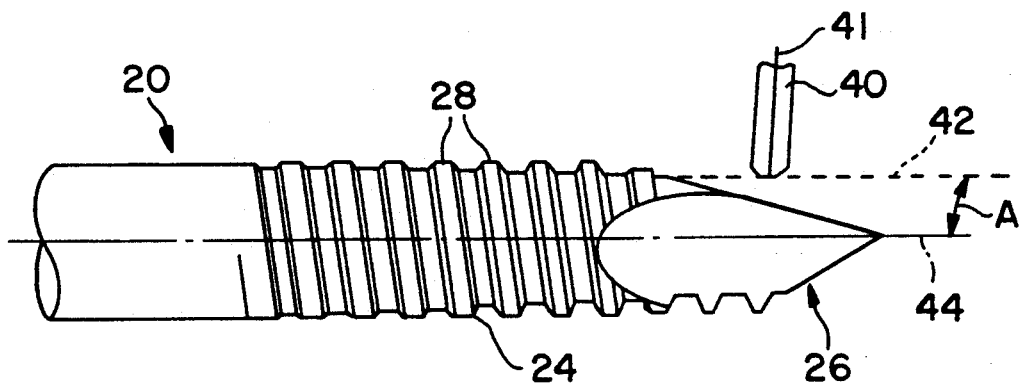
FIG. 3 is an illustration of a method of forming threads on the guide pin shown in FIG. 2.

FIG. 3 illustrates one method of forming threaded portion 24 on guide pin 20 using a standard cutting tool 40. Guide pin 20 is rotated along its longitudinal axis 44 by a standard apparatus (not shown) as cutting tool 40 moves along axis 42 to engage pin 20. With pin 20 continuing to rotate, cutting tool 40 travels along pin 20 at a constant speed, thereby forming threads 28. Once threads 28 are formed, drill end 26 is formed in a well known manner using a standard machine tool. Alternatively, drill end 26 may be formed before threads 28 are formed. The number of threads 28 can be varied by varying both the speed at which pin 20 is rotated and/or the speed with which cutting tool 20 is moved. It should be noted that FIG. 3 illustrates pin 20 with threads 28 already formed.

The path or line 42 along which cutting tool 40 travels forms an angle A of 2.5 degrees with longitudinal axis 44 of pin 20. The longitudinal axis 41 of cutting tool 40 is perpendicular to path 42. Since path 42 is not parallel to longitudinal axis 44, as cutting tool 40 forms threads 28, the distance between tool 40 and axis 44 of pin 20 will increase. This gradual movement of cutting tool 40 away from longitudinal axis 44 of pin 20 causes the root diameter of the threads being formed to gradually taper from the minimum value at the end of threaded portion 24 closest to drill end 26 to a maximum value that is equal to the diameter of shaft portion 22, as discussed above.

The tapering of the root diameter 30 results in the height of each thread 28 also tapering from a minimum value at the portion of threaded portion 24 closest to shaft 22 to a maximum height exhibited at the portion of threaded portion 24 closest to drill end 26. Referring to FIG. 2, the height of a thread 28 is defined as one half of the difference between the thread diameter 32 and the average of the root diameters on each axial side of the thread under consideration. This difference clearly increases as the threads approach drill end 26, where the threads become higher or more pronounced.

Figure 1:
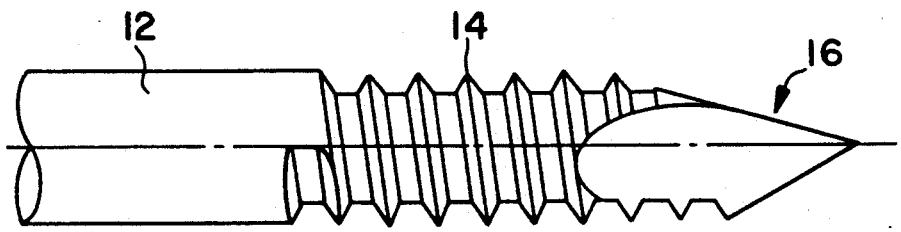
FIG. 1 is a side view of a prior art guide pin.

This gradual tapering of the root diameter of threaded portion 24 results in a smooth transition from the shaft diameter to the root diameter of threaded portion 24, resulting in a number of advantages over prior art guide pins. Prior art guide pins, like the pin shown in FIG. 1, have a sudden change in diameter at the junction of the threaded portion and the main shaft of the pin, which creates a weak point that may fail under stress. The guide pin of this invention exhibits a gradual change in root diameter and therefore includes no weak point, resulting in a number of advantages as described above.

The above description is intended for illustrative purposes only, and various modifications may be made within the scope of the appended claims as will be evident to one skilled in this art. For example, various thread shapes and drill points may be substituted for those illustrated. Similarly the number of threads may be varied, and the method of manufacture described above may be varied.

I claim:

1. A pin used to penetrate a bone comprising:
   an elongated shaft having a constant diameter; and
   an elongated threaded portion having a constant pitch comprising first and second axially separated ends, said first axial end being axially closer to said elongated shaft than said second axial end, said threaded portion having a root diameter that tapers from a maximum value at said first axial end to a minimum value at said second axial end and wherein said threaded portion has outer edges that gradually widen along the elongated axis from a minimum value at said second axial end to a maximum value at said first axial end.

2. The pin of claim 1 wherein said pin is a guide pin used to guide a cannulated bone screw.

3. The pin of claim 1 wherein said root diameter of said threaded portion tapers linearly from said first axial end to said second axial end.

4. The pin of claim 1 wherein said first axial end abuts said elongated shaft.

5. The pin of claim 1 further comprising a drill end extending axially from said second axial end of said threaded portion such that said drill end is connected to said elongated shaft by said threaded portion.

6. The pin of claim 1 wherein said root diameter at said first axial end of said threaded portion is substantially equal to said diameter of said elongated shaft.

7. The pin of claim 1 wherein said threaded portion comprises a plurality of threads, each of said threads having a thread height, wherein said thread height of said threads increases from said first axial end to said second axial end.

8. The pin of claim 6 wherein said thread height of said threads increases linearly from said first axial end to said second axial end.

9. The pin of claim 1 wherein said diameter of said elongated portion is equal to two millimeters.

10. The pin of claim 1 wherein said elongated threaded portion has a thread diameter that is equal to said diameter of said elongated shaft.

11. A pin used to penetrate a bone comprising:
an elongated shaft having a constant diameter;
an elongated threaded portion having a constant pitch comprising first and second axially separated ends, said first axial end being axially closer to said elongated shaft than said second axial end; and
a drill end extending axially from said second axial end of said threaded portion such that said drill end is connected to said elongated shaft by said threaded portion;
wherein said threaded portion has a root diameter that tapers linearly from a maximum value at said first axial end to a minimum value at said second axial end and wherein said threaded portion has outer edges that gradually widen along the elongated axis from a minimum value at said second axial end to a maximum value at said first axial end.

* * * * *